United States Patent
Rosiello

(10) Patent No.: US 7,824,558 B2
(45) Date of Patent: Nov. 2, 2010

(54) PROCESSING BAG FOR COMPONENT SEPARATOR SYSTEM AND METHOD OF REMOVING SEPARATED COMPONENTS

(75) Inventor: Keith M. Rosiello, Shrewsbury, MA (US)

(73) Assignee: Velico Medical, Inc., Beverly, MA (US)

( * ) Notice: Subject to any disclaimer, the term of this patent is extended or adjusted under 35 U.S.C. 154(b) by 0 days.

(21) Appl. No.: 11/474,739

(22) Filed: Jun. 26, 2006

(65) Prior Publication Data
US 2007/0225142 A1 Sep. 27, 2007

Related U.S. Application Data

(63) Continuation of application No. 10/211,143, filed on Aug. 2, 2002, now Pat. No. 7,074,172.

(51) Int. Cl.
*B04B 7/08* (2006.01)
*B01D 59/20* (2006.01)
*B04B 7/00* (2006.01)

(52) U.S. Cl. .............. 210/781; 210/782; 210/360.1; 494/10; 494/33; 494/43; 494/31; 494/45; 494/56; 494/21; 494/16

(58) Field of Classification Search .............. 494/10, 494/16, 31, 33, 43, 45, 56
See application file for complete search history.

(56) References Cited

U.S. PATENT DOCUMENTS

| | | | |
|---|---|---|---|
| 4,007,871 A * | 2/1977 | Jones et al. | 494/45 |
| 4,010,894 A * | 3/1977 | Kellogg et al. | 494/45 |
| 4,386,730 A | 6/1983 | Mulzet | |
| 4,387,848 A | 6/1983 | Kellogg et al. | |
| 4,767,396 A | 8/1988 | Powers | |
| 4,935,002 A | 6/1990 | Gordon | |
| 5,494,578 A * | 2/1996 | Brown et al. | 210/360.1 |
| 5,733,253 A | 3/1998 | Headley et al. | |
| 2002/0107131 A1 | 8/2002 | Jorgensen et al. | |
| 2002/0131891 A1 | 9/2002 | Smith et al. | |

* cited by examiner

*Primary Examiner*—Krishnan S Menon
(74) *Attorney, Agent, or Firm*—Foley & Lardner LLP; Michel Morency; James F. Ewing

(57) ABSTRACT

A centrifugal processing bag, system and method for separating the components of a mixed material is presented. The processing bag includes a hub and a first port for receiving the mixed material, where the first port includes an outlet positioned within the processing bag at a perimeter of the bag. The processing bag also including a second port having a second port inlet spaced proximate the hub and away from a central axis of the hub. The second port directs a separated material collected from the second port inlet out of the processing bag.

33 Claims, 10 Drawing Sheets

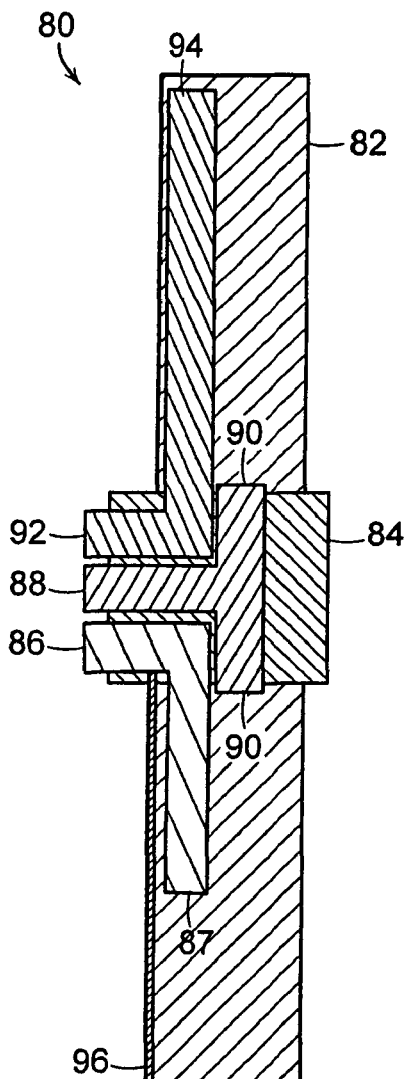
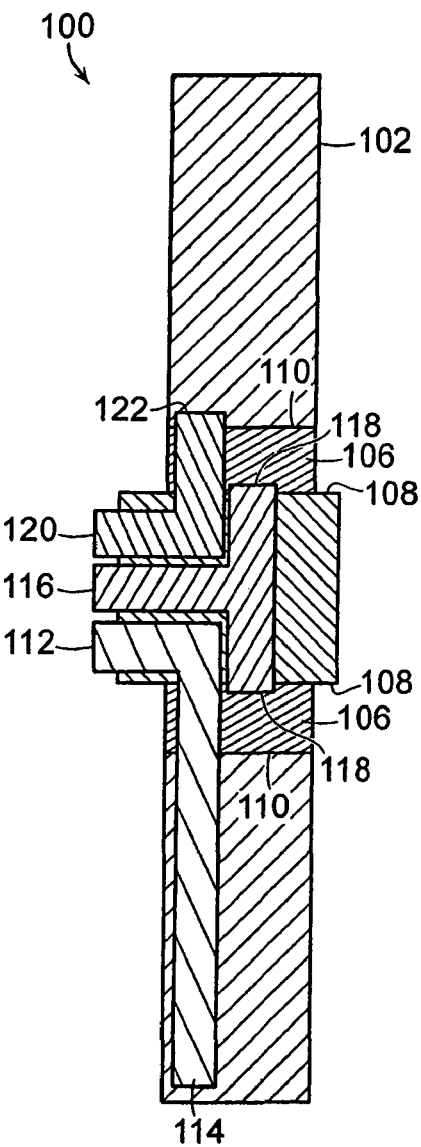
FIG. 4B
FIG. 5B

PROCESSING BAG FOR COMPONENT SEPARATOR SYSTEM AND METHOD OF REMOVING SEPARATED COMPONENTS

This Application is a Continuation of application Ser. No. 10/211,143, filed Aug. 2, 2002, now U.S. Pat. No. 7,074,172.

BACKGROUND OF THE INVENTION

1. Field of the Invention

The present invention relates in general to a component separations system, and more particularly to a system for separating blood components from whole blood. The principles of the present invention may be applied in a centrifuge processing system or other extracorporeal blood processing systems.

2. The Prior Art

Flexible processing chambers (bags) for processing biological cells in a fixed volume centrifuge, and methods for use of such processing bags, e.g., by centrifugation, are known. For example, PCT patent application PCT/US98/10406 describes a flexible cell processing chamber having a rotating seal to keep the contents of the chamber sterile during processing (see also U.S. Pat. No. 5,665,048. Flexible processing chambers advantageously are disposable and thus suitable for single-use sterile applications.

For certain applications, such as blood processing including blood component separation, enzymatic conversion of blood type, and pathogen inactivation of blood components, it is desirable to remove portions of material separated by process, both light material and/or heavy material. Simultaneous processing of multiple separated material from the processing bag reduces the time and expense required to perform such applications. Present flexible processing chambers do not provide the ability to perform independent simultaneous processing of multiple samples.

SUMMARY OF THE INVENTION

Accordingly, it is an object of the present invention to provide an improved component separator system that enables one or more components of a mixed material to be easily and continually separated using a centrifuge.

In one aspect of the present invention, a centrifugal processing bag for use with a component separator system for separating the components of a mixed material includes a hub and a first port for receiving the mixed material. The first port includes an outlet positioned within the processing bag at a perimeter of the bag. The processing bag also including a second port having a second port inlet spaced proximate the hub and away from a central axis of the hub. The second port directs a separated material collected from the second port inlet out of the processing bag.

In another aspect of the present invention, a centrifugal processing bag for use with a component separator system for separating the components of a mixed material is provided where the processing bag includes a hub having a first port for receiving the mixed material. The first port includes an outlet positioned within the processing bag proximate to the hub. The processing bag also includes a second port having a second port inlet positioned at a perimeter of the processing bag, where the second port directs a separated material collected from the second port inlet out of the processing bag.

In yet another aspect of the present invention, a centrifugal processing bag for use with a component separator system includes a hub having a first port for receiving the mixed material, where the first port includes an outlet positioned within the processing bag intermediate between the hub and a perimeter of the processing bag. The processing bag also includes a second port having a second port inlet positioned at a perimeter of the processing bag and a third port having a third port inlet positioned proximate the hub and spaced away from a central axis of the hub. The second port directs a first separated material collected from the second port inlet out of the processing bag and the third port directs a second separated material collected from the third port inlet out of the processing bag.

In yet another aspect of the present invention, a centrifugal processing bag for use with a component separator system includes a hub, a filter having an inlet portion and an outlet portion and a first port for receiving the mixed material. The first port includes an inlet positioned adjacent the hub and an outlet positioned within the processing bag at a perimeter of the bag. A second port is also included having a second port inlet positioned adjacent the inlet portion of the filter and a third port having an inlet positioned adjacent the outlet portion of the filter.

In yet another aspect of the present invention, a centrifugal processing bag for use with a component separator system includes a hub, a filter having an inlet portion and an outlet portion, a first port for receiving the mixed material having an outlet positioned adjacent the hub, a second port having a second port inlet positioned adjacent the inlet portion of the filter and a third port having an inlet positioned adjacent the outlet portion of the filter.

In still yet another aspect of the present invention, a centrifugal processing bag for use with a component separator system includes a hub, a first filter having an inlet portion and an outlet portion, a second filter having an inlet portion and an outlet portion, a first port for receiving the mixed material having an outlet positioned intermediate between a perimeter of the processing bag and the hub, a second port having a second port inlet positioned adjacent the inlet portion of the first filter, a third port having an inlet positioned adjacent the outlet portion of the first filter and a fourth port having an inlet positioned adjacent the outlet portion of the second filter.

In another aspect of the present invention, a method of separating components of a mixed material in solution includes providing a flow of a mixed material in solution to a centrifugal processing bag in a component separator system, where the processing bag includes a hub, a first port for receiving the mixed material and having an outlet positioned within the processing bag, a second port having a second port inlet positioned within the processing bag at a position to collect a separated material. The method also includes centrifuging the processing bag such that components of the mixed material are separated from one another, and establishing a second flow of separated material from the second port.

In yet another aspect of the present invention a method of separating components of a mixed material in solution includes providing a flow of a mixed material in solution to a centrifugal processing bag in a component separator system, where the processing bag includes a hub having a first port for receiving the mixed material and having an outlet positioned within the processing bag, a second port having a second port inlet positioned within the processing bag and a third port having a third port inlet positioned within the processing bag. The method also includes centrifuging the processing bag such that components of the mixed material are separated from one another, establishing a second flow of first separated material from the second port and establishing a third flow of second separated material from the third port.

In yet another aspect of the present invention, a method of separating components of a mixed material in solution includes providing a flow of a mixed material in solution to a centrifugal processing bag in a component separator system, where the processing bag includes a hub, a filter having an inlet portion and an outlet portion, a first port for receiving the mixed material and having an outlet positioned within the processing bag, a second port having a second port inlet positioned within the processing bag, and a third port having a third port inlet positioned within the processing bag. The method further includes centrifuging the processing bag such that components of the mixed material are separated from one another, establishing a second flow of first separated material from the second port and establishing a third flow of second separated material from the third port.

BRIEF DESCRIPTIONS OF THE DRAWINGS

Numerous other objects, features and advantages of the invention should now become apparent upon a reading of the following detailed description when taken in conjunction with the accompanying drawings, in which:

FIG. 4B is a side, cross-sectional view of a processing bag for a component separator system according to a third embodiment of the present invention.

FIG. 5B is a side, cross-sectional view of a processing bag for a component separator system according to a third embodiment of the present invention.

DETAILED DESCRIPTION OF THE PREFERRED EMBODIMENTS

The drawings, that are to be discussed hereinafter, illustrate a processing chamber/bag for receiving a mixed material for separation. In particular, a preferred embodiment of this invention is directed to separating blood components of whole blood and directing them out of the processing bag.

Figure 1:
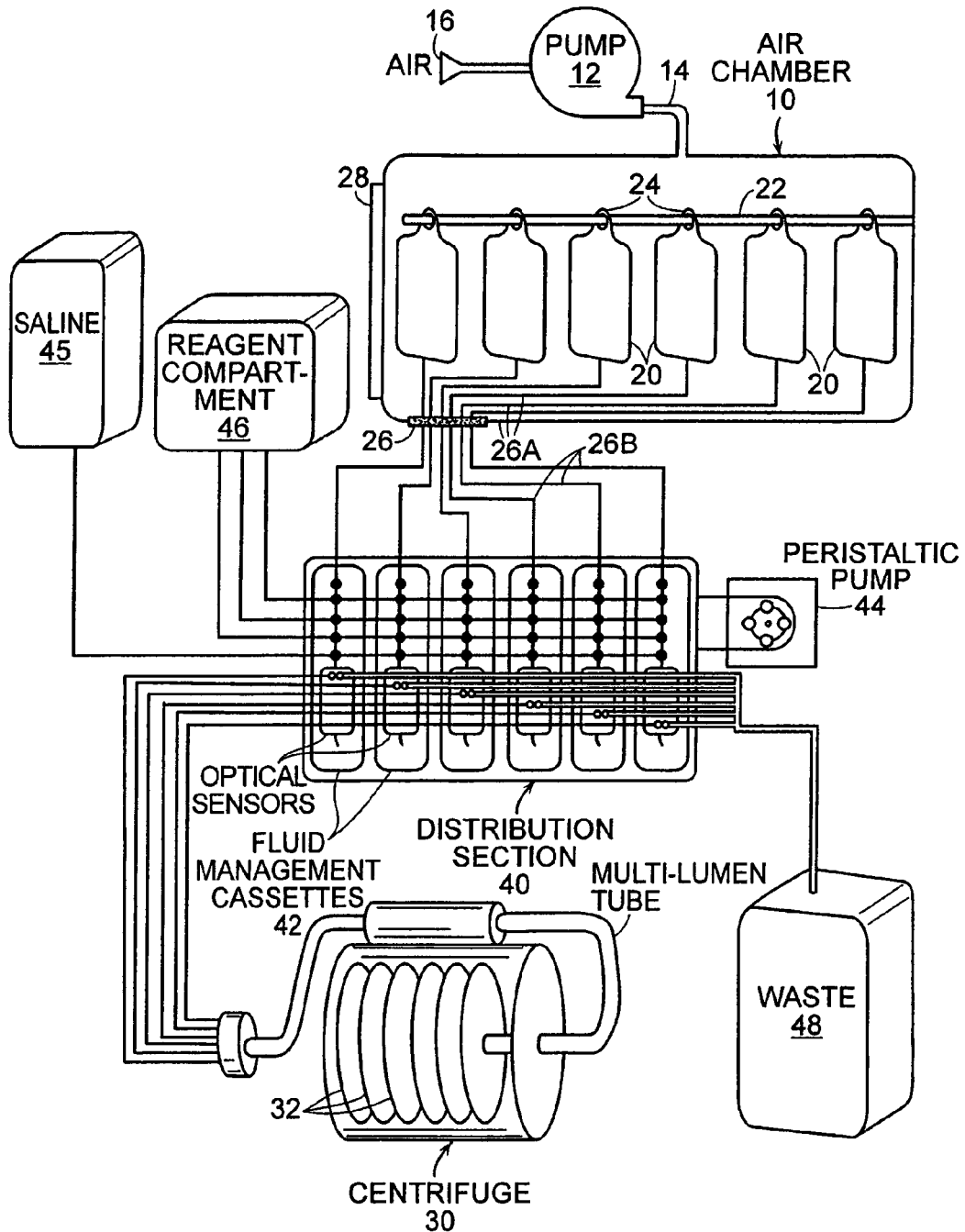
FIG. 1 is a system block diagram illustrating a system in which the blood product transfer apparatus of the present invention may be employed.

Reference is now made to FIG. 1 which is a system block diagram of a centrifugal, blood processing system embodying the device for enabling transfer of blood product between at least one blood storage bag and a centrifuge processing bag. Many of the components illustrated in FIG. 1 are not described in detail herein. However, reference is made to U.S. Pat. No. 6,175,420 to Barry et al., granted Jan. 16, 2001 for a more comprehensive description of fluid management portions of the system. Reference may also be made to U.S. Pat. No. 5,665,048 to Jorgensen, granted Sep. 9, 1997 for further descriptions relating to the centrifuge itself. Both U.S. Pat. Nos. 5,665,048 and 6,175,420 are incorporated herein by reference, in their entirety.

FIG. 1 illustrates the vacuum/pressure chamber 10 in accordance with the present invention and the associated pump 12 that couples to the airtight containment chamber 10 by way of the tubing 14. FIG. 1 also illustrates the air supply at 16. Schematically illustrated within the chamber 10 are a series of blood product storage bags 20. Each of these bags is supported from a hanger 22 by means of a securing loop 24 associated with each bag. Individual lines or tubing from each bag couples through the wall of the chamber by way an airtight fixture 26. FIG. 1 illustrates this fixture at the bottom of the chamber 10. However, in embodiments to be described in further detail hereinafter, the fixture is usually provided on the door end and at about a mid-level position in the door.

In FIG. 1 there is also illustrated a centrifuge 30 that may have associated therewith centrifuge processing bags 32. Also illustrated is the distribution section 40 comprising a plurality of fluid management cassettes 42 and a peristaltic pump 44. Also coupling to the cassettes 42 is a saline supply or bag 45 and reagent compartment 46. Also illustrated is a waste bag 48 relating to the fluid management cassettes.

Not specifically illustrated in FIG. 1, but considered as part of the system, is a computer controller, such as a processor control 50 that controls, inter alia, operation of the components of the system in accordance with the present invention.

FIGS. 2A-7B illustrate blood processing bags according to the various embodiments according to the present invention, each of which is described below. For each embodiment, mixed material 2 is introduced into the blood processing bag and is separated into various components including light material component(s) 4 and heavy material component(s) 6. Accordingly, after a predetermined period of time passes after initiation of centrifugation, an interface 8a between the mixed material 2 and light separated material 4 and an interface 8b between the mixed material 2 and the heavy separated material 6 exist. The interfaces are specifically illustrated in FIG. 2, but FIGS. 3-7 also include such interfaces.

These interfaces may be used to control processing (via the controller 50) and the flow of mixed material into the processing bag and separated material out, and are detected by an interface detection sensor 96 as shown in FIGS. 4 and 7, positioned external or internal to the bag.

Figure 2A:
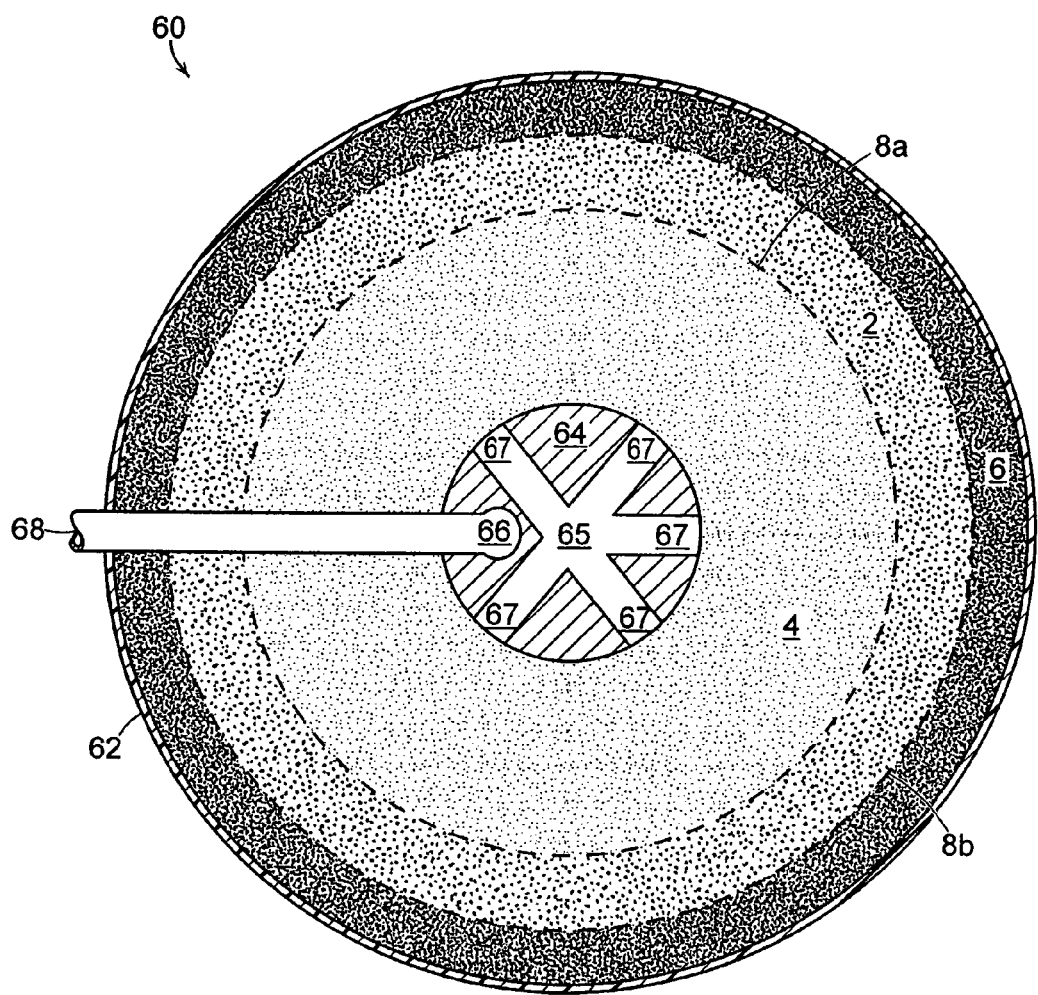
FIG. 2A is a cross-sectional view of a processing bag for a component separator system according to a first embodiment of the present invention.
Figure 2B:
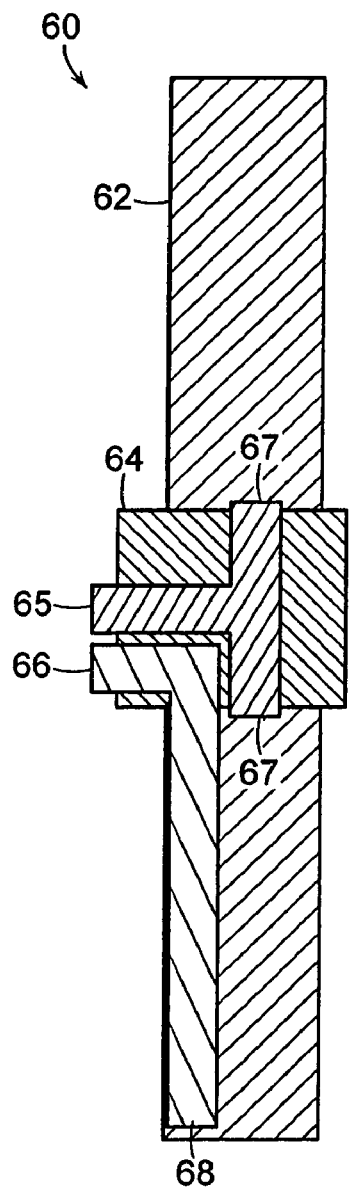
FIG. 2B is a side, cross-sectional view of a processing bag for a component separator system according to a first embodiment of the present invention.

Accordingly, FIGS. 2A and 2B illustrates a cross-sectional view of a centrifuge processing bag 60 according to a first embodiment of the present invention. In this embodiment, lighter material/fluid separated from the mixed material, while heavier material is retained. Moreover, to dilute, wash and/or process the heavy fluid, a solution that is lighter than the heavy material may be run through the heavy material.

The processing bag 60 includes a bag 62 manufactured of a plastic material or the like, having a central hub 64. The central hub houses a first port 66, which is connected to an inlet 68 positioned at a perimeter of the processing bag. The first port may receive the mixed material (i.e., whole blood) in a continuous flow and directs the received material to the perimeter of the processing bag.

A second port 65 is also included on the hub, which is connected to one or more inlets 67 positioned around a perimeter of the hub. Thus, as the centrifuge spins, and the components of the blood begin to separate, a lighter blood component accumulates near the inlets 67 to the second ports and a heavier blood component accumulates near the perimeter of the processing bag.

Figure 3B:
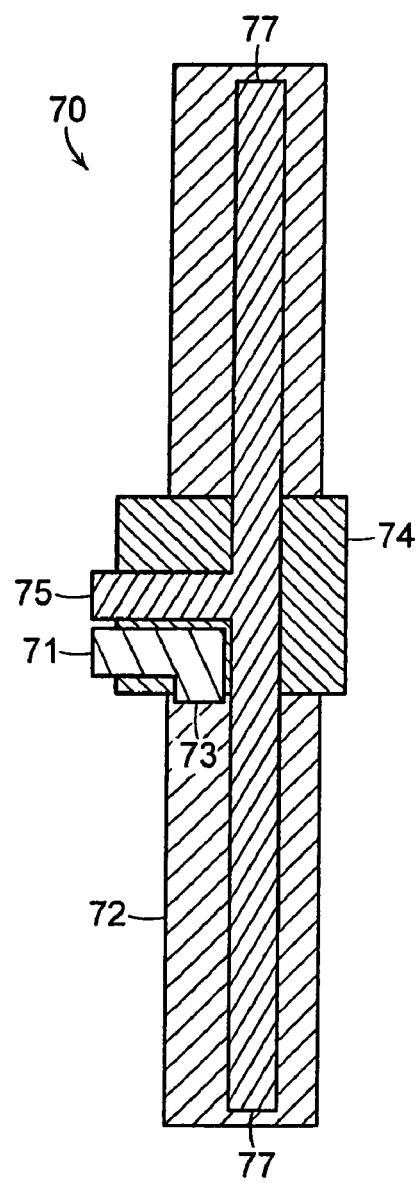
FIG. 3B is a side, cross-sectional view of a processing bag for a component separator system according to a first embodiment of the present invention.
Figure 3A:
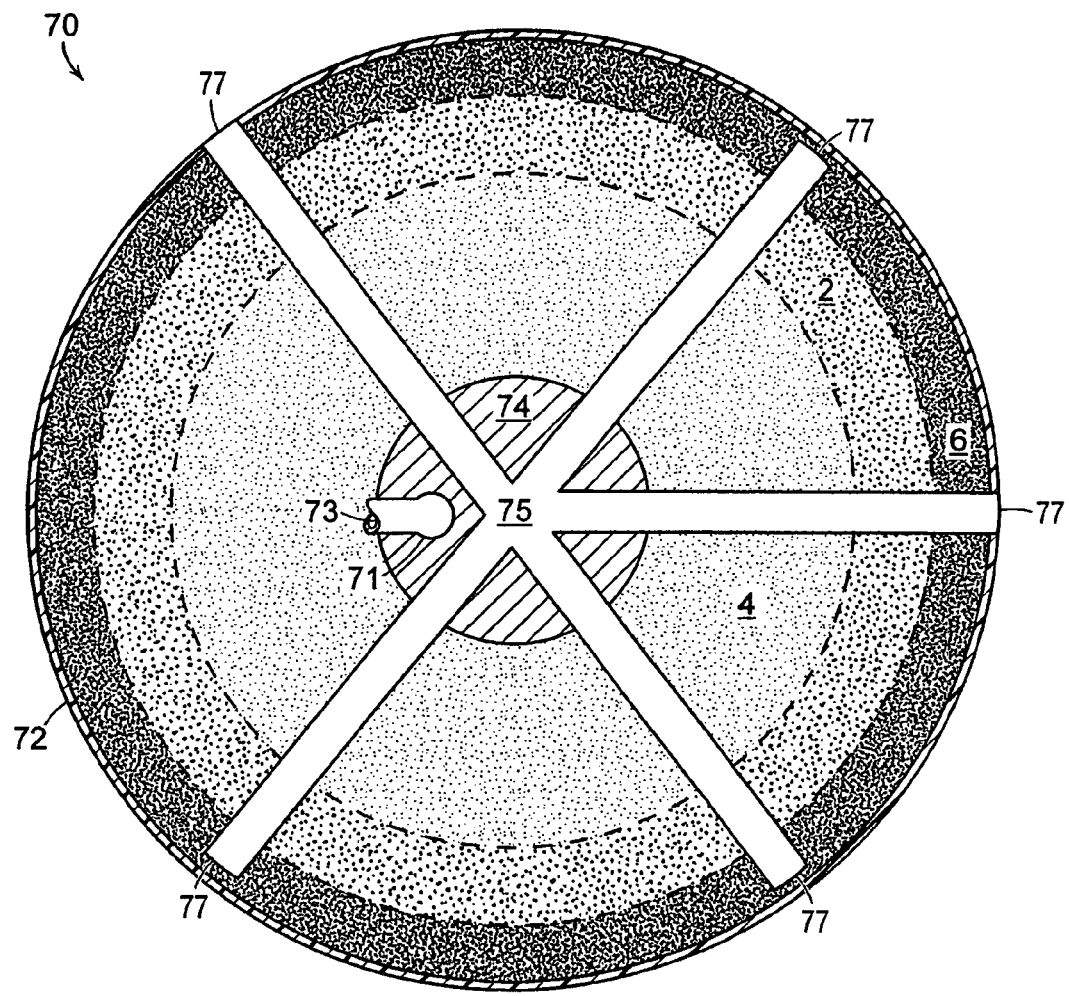
FIG. 3A is a cross-sectional view of a processing bag for a component separator system according to a second embodiment of the present invention.

FIGS. 3A and 3B illustrates a second embodiment according to the present invention. In this embodiment, heavier material/fluid is removed from the mixed material in the processing bag while retaining light material/fluid.

As shown, a processing bag 70 includes a plastic bag 72 having a central hub 74 including a first port 71 for receiving mixed material to separate and a second port 75 for directing a separated material out of the processing bag.

In contrast to the first embodiment, the outlet 73 of the first port 71 within the processing bag is positioned adjacent the hub and the second port 75 is connected to an inlet(s) 77 positioned at the perimeter of the processing bag in the second embodiment, so as to direct a heavier separated component away from the processing bag.

One of ordinary skill in the art will appreciate that a solution that is heavier than the light material separated from the mixed material maybe run through the light material to dilute, wash and/or process the light material.

A third embodiment of the present invention is illustrated in FIG. 4. In this embodiment, both light and heavy separated materials may be removed from the processing bag. In addition, as discussed with the previous two embodiments, a lighter solution, that is lighter than heavy separated material, may be run through the heavy material and a solution that is heavier than the light material may be run through the light material to dilute, wash, and/or process the respective fluid.

Figure 4A:
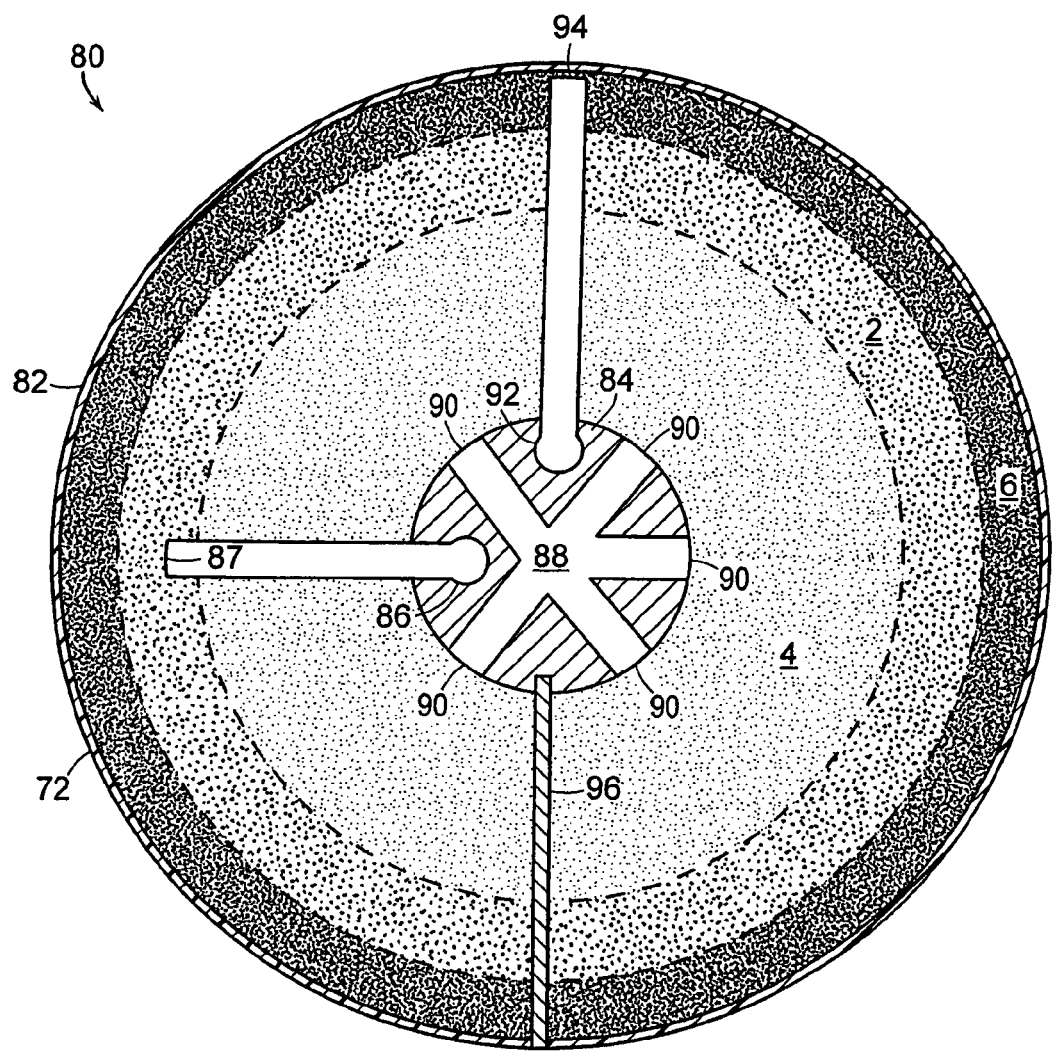
FIG. 4A is a cross-sectional view of a processing bag for a component separator system according to a third embodiment of the present invention.

Accordingly, a processing bag 80 shown in FIGS. 4A and 4B includes a bag 82, and a hub 84 which includes a plurality of ports. A first port 86 of the plurality of ports receives mixed material for separation in the processing bag and is connected to an outlet 87 which is positioned intermediate in the processing bag between the hub and perimeter. A second port 88 directs a lighter separated material from the processing bag and may include a plurality of inlets 90 positioned adjacent the hub. The processing bag also includes a third port 92 for directing a heavier separated material away from the perimeter of the processing bag via an inlet 94.

Mixed material is introduced into the processing bag via the first port/outlet, and then is centrifugally separated. The light separated material departs the processing bag via the second port and the heavy separated material departs the processing bag via the third port.

The number of inlets to the second and third ports is also variable, where a single or multiple inlets may be used depending upon design. Thus, as shown, the second port is in communication with inlets 90, and third port 92 is in communication with a single inlet 94 ports.

The interface detector 96 may be used to locate the interface between separated and mixed materials, and is used to maintain (in conjunction with an expressor system) proper separation and operational parameters for the component separator system.

Figure 5A:
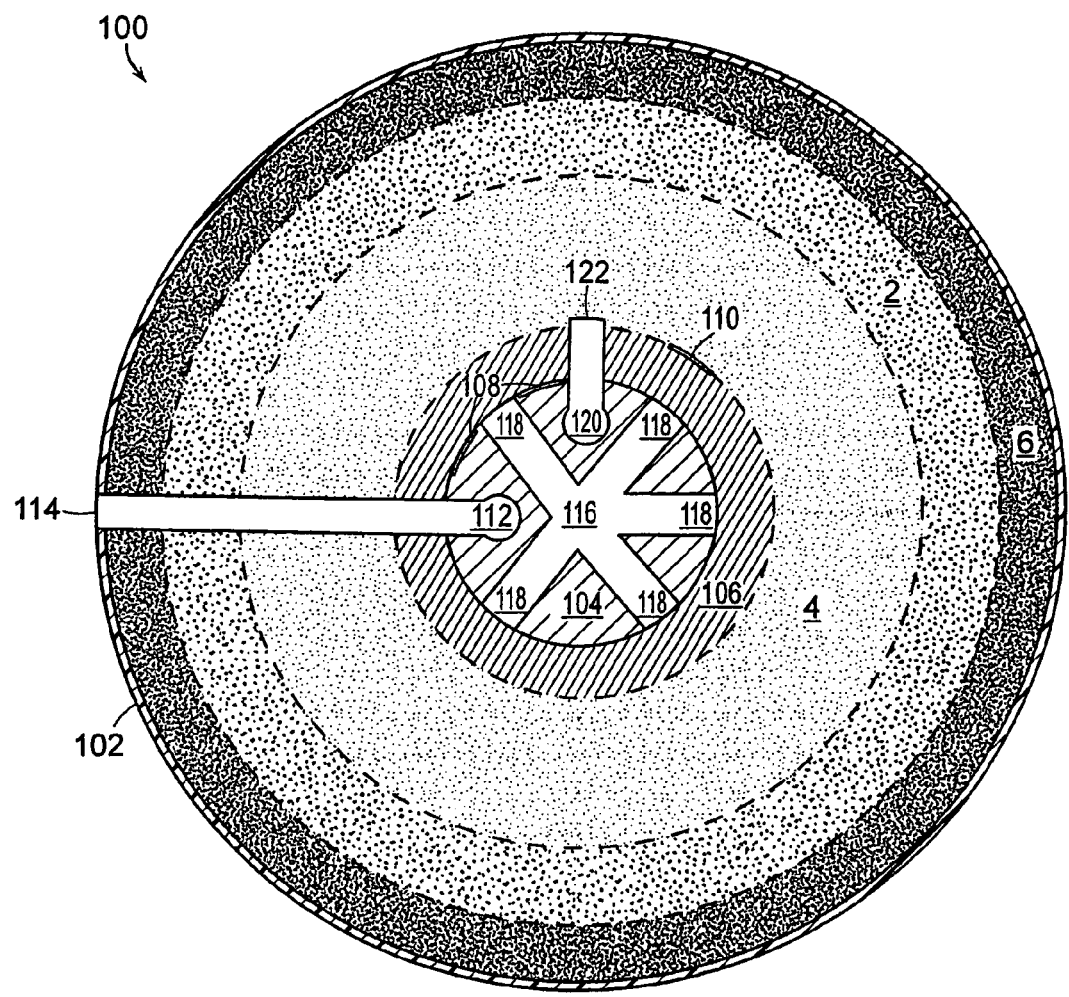
FIG. 5A is a cross-sectional view of a processing bag for a component separator system according to a fourth embodiment of the present invention.

FIGS. 5A and 5B illustrates a fourth embodiment according to the present invention. In this embodiment, the processing bag separates and filters light material/fluid from mixed material. Accordingly, the processing bag 100 according to this embodiment includes a bag 102 having a hub 104. The hub, as with the previous embodiments, includes one or more ports for directing material into and/or out of the processing bag. A filter material 106 having an outlet portion 108 positioned adjacent the hub and an inlet portion 110 facing a remainder of the processing bag.

The hub also includes a first port 112 having an outlet 114 for introducing a mixed material into the processing bag. The outlet of the first port in this embodiment is positioned at a point on the perimeter of the processing bag. A second port 116 includes a plurality of inlets 118 positioned adjacent the outlet portion 108 of the filter material. Thus, lighter separated material may depart the processing bag via the second port 116 after being filtered through the filter material.

A third port 120 includes an inlet 122 positioned at the inlet portion of the filter material. Accordingly, unfiltered, separated light material may depart the processing bag via the third port.

Figure 6:
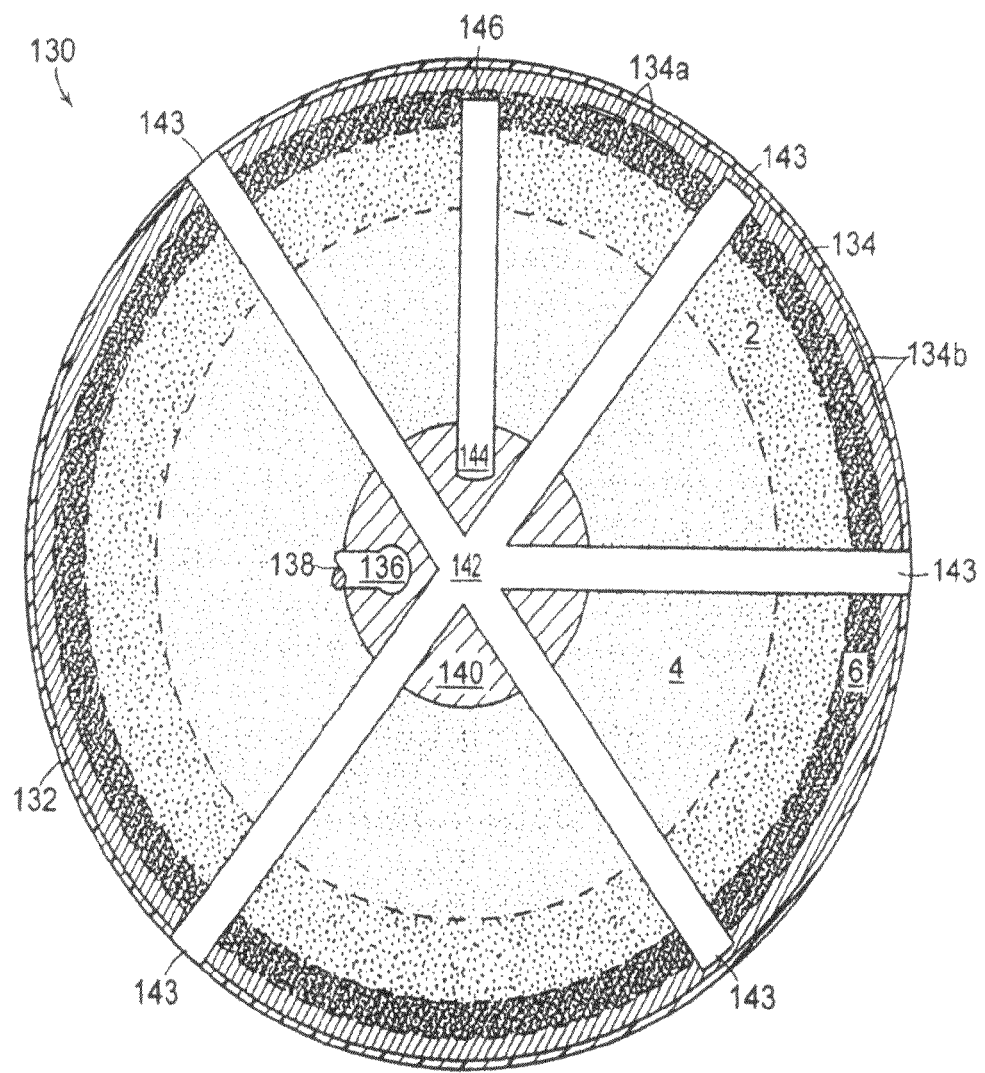
FIG. 6A is a cross-sectional view of a processing bag for a component separator system according to a fifth embodiment of the present invention.
FIG. 6B is a side, cross-sectional view of a processing bag for a component separator system according to a third embodiment of the present invention.
Figure 6B:
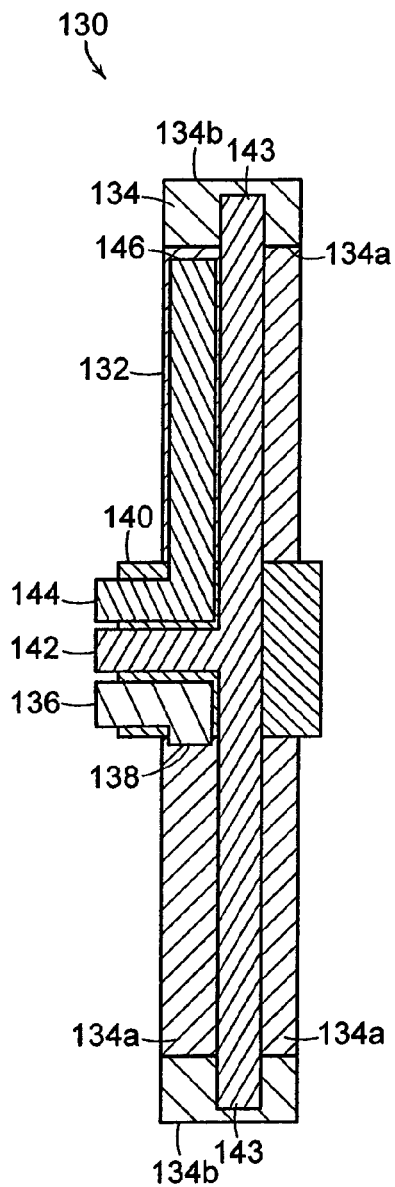

A fifth embodiment 130 of the present invention is illustrated in FIGS. 6A and 6B. This embodiment allows separated heavy material to be filtered (or unfiltered) and removed from the processing bag. As shown, a filter material 134 is positioned along a perimeter of the processing bag 132 and includes an inlet portion 134a comprising the inner diameter of the filter material and an outlet portion 134b comprising the outer diameter of the filter material. A first port 136 receives the mixed material for separation, which is introduced into the processing bag via the first port outlet 138 positioned proximate to a hub 140 at the center of the processing bag. A second port 142 includes a plurality of inlets 143 (although one inlet is sufficient) positioned adjacent the outlet portion 134b of the filter material 134. A third port 144 includes an inlet 146 positioned adjacent the inlet portion 134a of the filter material 134.

Thus, the second port enables filtered heavy, separated material via the second port inlet to depart the processing bag, with the third port enabling unfiltered, separated material via the third port inlet to depart the processing bag.

Figure 7B:
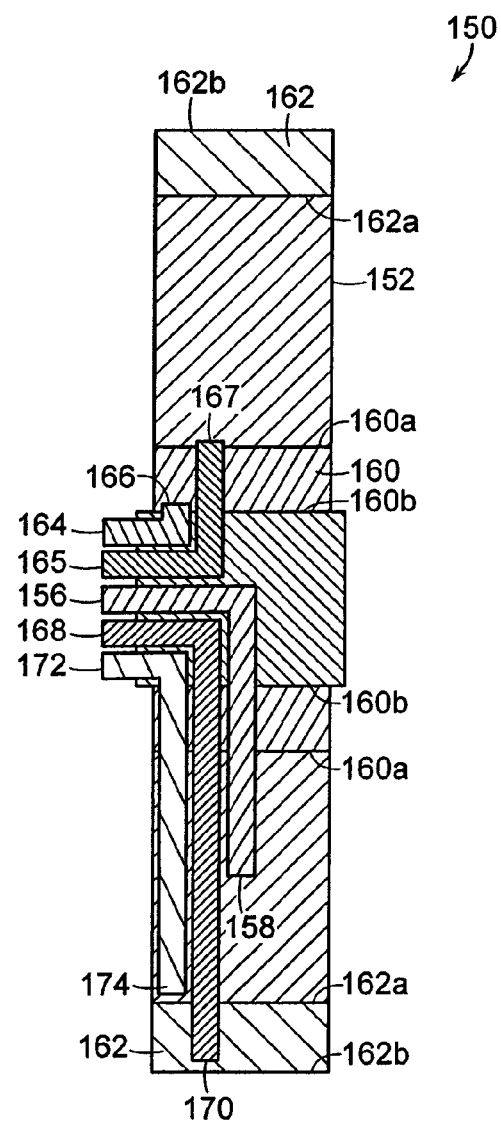
FIG. 7B is a side, cross-sectional view of a processing bag for a component separator system according to a third embodiment of the present invention.
Figure 7A:
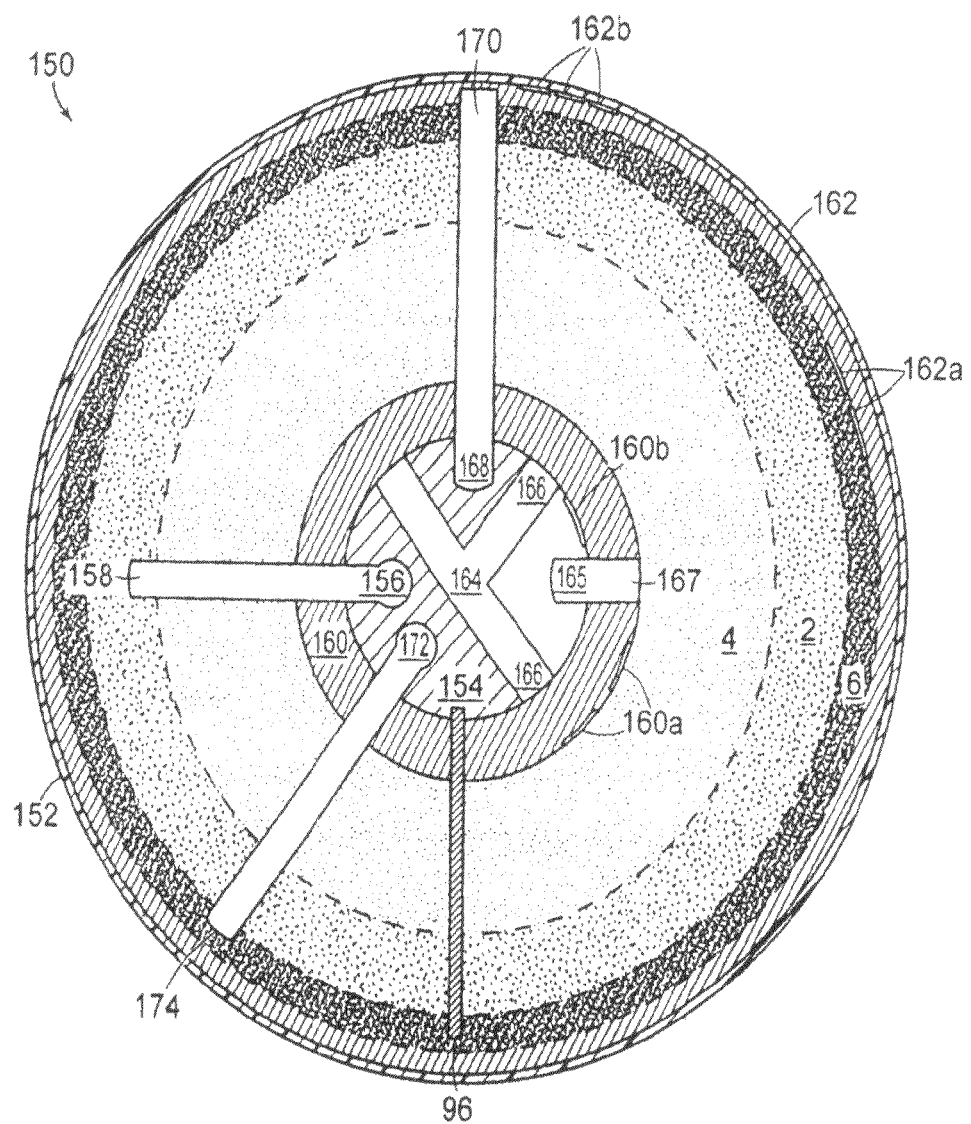
FIG. 7A is a cross-sectional view of a processing bag for a component separator system according to a sixth embodiment of the present invention.

FIGS. 7A and 7B illustrates yet a sixth embodiment according to the present invention in which both heavy and light separated material may be removed from the processing bag. Thus, processing bag 150 includes the bag 152 having central hub 154 which includes access ports for introducing and removing materials from the processing bag. As with the previous aspects, a first port 156 introduces mixed material into the processing bag via a first port outlet 158 positioned intermediate in the processing bag between the perimeter of the bag and the hub. A first filter material 160, having an inlet portion 160a and an outlet portion 160b is positioned immediately adjacent the hub.

The processing bag also includes a second filter material 162 positioned along the perimeter of the processing bag, which includes an inlet portion 162a comprising an inner circumference of the filter material facing in a direction toward the hub of the processing bag and an outlet portion 162b, comprising an outer circumference of the filter material facing in a direction toward the perimeter of the processing bag.

A second port 164 includes one or more inlets 166, which are positioned adjacent the outlet portion 160b of the first filter material, so that filtered, light material separated from the processing bag. A third port 168 includes an inlet 170 positioned adjacent the outlet portion 162b, to collect filtered, heavy separated material. Additionally, a fourth port 172, having an inlet 174 positioned adjacent the inlet portion 162a of the second filter material, allows unfiltered, separated, heavy material depart the processing bag.

A fifth port 165 includes inlet 167 which collects unfiltered light material separated during processing can be retrieved from the bag.

In each of the above embodiments mixed material, for example, whole blood, is introduced into the processing bag, through the first port, centrifuged, and expressed out of the processing bags through various ports to obtain various separated materials, and through various methods (examples given below). In addition, a solution that is lighter than a heavier separated material may be introduced into the processing bag via the first port and first port outlet, to dilute, wash and/or process the heavy material (when collecting, for example, light separated material). Likewise, a solution that is heavier than the light material through the light material to dilute, wash, and/or process light, separated material (when collecting, for example, heavy, separated material). In systems in which both heavy and light separated material is processed and removed from the processing bag, both light and heavy solutions may be used to dilute, wash and/or process the heavy and light separated material, respectively.

In order to remove separated material components from the processing bag according to the embodiments described above, a variety of methods may be used. For example, separated material may be removed from the processing bag by using a processing bag of fixed volume, and controlling the volume of material introduced into the bag. In addition, the volume of the processing bag may be controlled, through various methods, to allow mixed material into the bag and separated material out of the bag. To assist in removing separated materials from the processing bag, the interface detection sensor, positioned either internal or external to the processing bag may also be used so that adequate control of the separated material may be had. The interface detection sensor, in combination with the controller according to the present invention, determines how much of separated material exists at one time in the processing bag.

Alternatively, expressor bags, as disclosed in co-pending U.S. patent application Ser. No. 09/970,547, filed Oct. 3, 2001 (the disclosure of which is herein incorporated by reference). Accordingly, expressor bags positioned adjacent the processing bag are inflated (via gas or liquid) to press against the processing bag and force out material stored therein. Other processing methods familiar to those of skill in the art may also be used.

The present invention has numerous applications in the biotechnology and medical fields. In general, the present invention and component separator system design can be applied to any industry where separation is a requirement. Accordingly, examples of such applications include:

Biotechnology
Separation of components from bioreactors and bio-fermentation processes;
separation and processing of materials in waste management; and
general extraction, purification and concentration of materials for industry use.
Medical
Cell washing;
enzymatic conversion of red cell to ECO;
pathogen inactivation;
glycosylation;
lipid filtration;
leukocyte reduction;
inter-operative cell salvage;
cryo-preservation;
de-glycerolization;
blood component separation; and
apheresis (red cell, plasma, platelets).

The embodiments presented are for use both single unit (processing bag or system) and multiple simultaneous unit (processing bag) processing apparatuses when considered with the referenced patents and patent applications. Moreover, a plurality of processing bags may be used as independent, simultaneous processors that work in parallel or can be sequenced such that processes that require more than one bag can be run serially in two or more adjacent or non-adjacent processing bags.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of separating components of a mixed material in solution comprising:
providing a first flow of a mixed material in solution to a flexible centrifugal processing bag in a component separator system,
said centrifugal processing bag having a continuous interior processing volume, and comprising
a hub having a central axis,
a first port for receiving said mixed material, wherein said first port includes an outlet positioned within the continuous interior processing volume of said centrifugal processing bag and spaced apart from the central axis a first distance,
a second port having a second port inlet positioned within the continuous interior processing volume of said centrifugal processing bag and spaced apart from said central axis a second distance, wherein the second distance is different from the first distance, said second port for directing a separated material collected from said second port inlet out of said centrifugal processing bag; and
a flexible portion extending radially outward in a direction transverse the central axis from the hub to an uninterrupted circular outer perimeter of said centrifugal processing bag;
centrifuging said centrifugal processing bag such that at least one component of said mixed material is separated along the uninterrupted circular outer perimeter of said centrifugal processing bag; and
establishing a second flow of separated material from said second port.

2. The method according to claim 1, wherein said second flow is established by controlling a volume of said mixed material.

3. The method according to claim 1, wherein said second flow is established by controlling the weight of said centrifugal processing bag having said mixed material.

4. The method according to claim 1, wherein said second flow is established by varying the volume of said centrifugal processing bag.

5. The method according to claim 4, further comprising determining an interface between a separated material and said mixed material.

6. The method according to claim 5, wherein said interface is detected using a sensor placed external to said centrifugal processing bag.

7. The method according to claim 5, wherein said interface is detected using a sensor placed internal to said centrifugal processing bag.

8. The method according to claim 1, wherein said first flow of a mixed material is provided to a plurality of centrifugal processing bags in said component separator system, each said centrifugal processing bag comprising a hub having a central axis, a first port for receiving said mixed material, wherein said first port includes an outlet positioned within said centrifugal processing bag and spaced apart from the central axis a first distance, and a second port having a second port inlet positioned within said centrifugal processing bag and spaced apart from said central axis a second distance, wherein the second distance is different from the first distance, said second port for directing a separated material collected from said second port inlet out of said centrifugal processing bag.

9. A method of separating components of a mixed material in solution comprising:

providing a first flow of a mixed material in solution to a flexible centrifugal processing bag in a component separator system, said centrifugal processing bag having a continuous interior processing volume and comprising a hub having a central axis, and a first port for receiving said mixed material, wherein said first port includes an outlet positioned within the continuous interior processing volume of said centrifugal processing bag and spaced apart from the central axis a first distance, said centrifugal processing bag also including a flexible portion extending radially outward in a direction transverse the central axis from the hub to an uninterrupted circular outer perimeter of said centrifugal processing bag a second port having a second port inlet positioned within the continuous interior processing volume of said centrifugal processing bag and spaced apart from said central axis a second distance, wherein the second distance is different from the first distance, said second port for directing a second flow of first separated material collected from said second port inlet out of said centrifugal processing bag, and a third port having a third port inlet positioned within the continuous interior processing volume of said centrifugal processing bag and spaced apart from said central axis a third distance, wherein the third distance is different from the first distance and the second distance, said second port for directing a third flow of second separated material collected from said third port inlet out of said centrifugal processing bag;

centrifuging said centrifugal processing bag such that at least one component of said mixed material is separated along the uninterrupted circular outer perimeter of said centrifugal processing bag; and establishing the second flow of first separated material from said second port; and establishing the third flow of second separated material from said third port.

10. The method according to claim 9, wherein said first flow of said mixed material is provided to a plurality of centrifugal processing bags in said component separator system, each said centrifugal processing bag comprising a hub having a central axis, and a first port for receiving said mixed material, wherein said first port includes an outlet positioned within said centrifugal processing bag and spaced apart from the central axis a first distance, said centrifugal processing bag also including a second port having a second port inlet positioned within said centrifugal processing bag and spaced apart from said central axis a second distance, wherein the second distance is different from the first distance, and a third port having a third port inlet positioned within said centrifugal processing bag and spaced apart from said central axis a third distance, wherein the third distance is different from the first distance and the second distance.

11. The method according to claim 9, wherein said second flow and said third flow are established by controlling a volume of said mixed material.

12. The method according to claim 9, wherein said second flow and said third flow arc established by controlling the weight of said centrifugal processing bag having said mixed material.

13. The method according to claim 9, wherein said second flow and said third flow are established by varying the volume of said centrifugal processing bag.

14. The method according to claim 9, further comprising determining an interface between a separated material and said mixed material.

15. The method according to claim 14, wherein said interface is detected using a sensor placed external to said centrifugal processing bag.

16. The method according to claim 14, wherein said interface is detected using a sensor placed internal to said centrifugal processing bag.

17. A method of separating components of a mixed material in solution comprising:

providing a first flow of a mixed material in solution to a flexible centrifugal processing bag in a component separator system, said centrifugal processing bag having a continuous interior processing volume and comprising a hub having a central axis, a flexible portion extending radially outward in a direction transverse the central axis from the hub to an uninterrupted circular outer perimeter of said centrifugal processing bag;

a filter having an inlet portion and an outlet portion, a first port for receiving said mixed material, wherein said first port includes an outlet positioned within the continuous interior processing volume of said centrifugal processing bag and spaced apart from the central axis a first distance, a second port having a second port inlet positioned within the continuous interior processing volume of said centrifugal processing bag and spaced apart from said central axis a second distance, wherein the second distance is different from the first distance, and a third port having a third port inlet positioned within the continuous interior processing volume of said centrifugal processing bag and spaced apart from said central axis a third distance, wherein the third distance is different from the first distance and the second distance;

centrifuging said centrifugal processing bag such that at least one component of said mixed material is separated along the uninterrupted circular outer perimeter of said centrifugal processing bag;

establishing a second flow of first separated material from said second port; and establishing a third flow of second separated material from said third port.

18. The method according to claim 17, wherein a flow of a mixed material is provided to a plurality of centrifugal processing bags in a component separator system, each said centrifugal processing bag comprising a hub having a central axis, a filter having an inlet portion and an outlet portion, a first port For receiving said mixed material, wherein said first port includes an outlet positioned within said processing bag and spaced apart from the central axis a first distance, a second port having a second port inlet positioned within said centrifugal processing bag and spaced apart from said central axis a second distance, wherein the second distance is different from the first distance, and a third port having a third port inlet positioned within said centrifugal processing bag and spaced apart from said central axis a third distance, wherein the third distance is different from the first distance and the second distance.

19. The method according to claim 17, wherein said second flow and said third flow are established by controlling a volume of said mixed material.

20. The method according to claim 17, wherein said second flow and said third flow are established by controlling the weight of said centrifugal processing bag having said mixed material.

21. The method according to claim 17, wherein said second flow and said third flow are established by varying the volume of said centrifugal processing bag.

22. The method according to claim 17, further comprising determining an interface between a separated material and said mixed material.

23. The method according to claim 22, wherein said interface is detected using a sensor placed external to said centrifugal processing bag.

24. The method according to claim 22, wherein said interface is detected using a sensor placed internal to said centrifugal processing bag.

25. The method according to claim 17, wherein said second port inlet is positioned adjacent said inlet portion of said filter and said third port inlet is positioned adjacent said outlet portion of said filter.

26. The method according to claim 1, said centrifugal processing bag further comprising a third port having a third port inlet and a first filter having an inlet portion and an outlet portion, wherein said second port inlet is positioned adjacent said inlet portion of said first filter and said third port inlet is positioned adjacent said outlet portion of said first filter.

27. The method according to claim 9, said centrifugal processing bag further comprising a first filter having an inlet portion and an outlet portion, wherein said second port inlet is positioned adjacent said inlet portion of said first filter and said third port inlet is positioned adjacent said outlet portion of said first filter.

28. The method according to claim 1, further comprising introducing via the first port outlet a solution having a lighter weight than the separated material to process the separated material.

29. The method according to claim 1, further comprising introducing via the first port outlet a solution having a heavier weight than the separated material to process the separated material.

30. The method according to claim 1, further comprising introducing via the first port outlet a solution having a lighter weight than the separated material to wash the separated material.

31. The method according to claim 1, further comprising introducing via the first port outlet a solution having a heavier weight than the separated material to wash the separated material.

32. The method according to claim 1, further comprising collecting via a filtered port an introduced solution.

33. The method according to claim 1, further comprising:
introducing via the first port outlet a solution having a different weight than the separated material to dilute, wash, and/or process the separated material; and
collecting via a filtered port the introduced solution.

* * * * *

UNITED STATES PATENT AND TRADEMARK OFFICE
CERTIFICATE OF CORRECTION

PATENT NO.         : 7,824,558 B2                                    Page 1 of 1
APPLICATION NO.    : 11/474739
DATED              : November 2, 2010
INVENTOR(S)        : Keith M. Rosiello It is certified that error appears in the above-identified patent and that said Letters Patent is hereby corrected as shown below:

In column 10, line 31, please delete the word "arc" and insert the word --are-- therefor.

Signed and Sealed this
Eighteenth Day of January, 2011

David J. Kappos
*Director of the United States Patent and Trademark Office*